United States Patent [19]

Schaefer

[11] Patent Number: 4,891,441

[45] Date of Patent: Jan. 2, 1990

[54] PROCESS FOR THE PREPARATION OF POLYMERIC TERTIARY ARALKYL ISOCYANATES FROM 1,3- OR 1,4-BIS(1-CHLORO-1-METHYLETHYL)BENZENE

[75] Inventor: Frederic C. Schaefer, Columbia, S.C.

[73] Assignee: American Cyanamid, Stamford, Conn.

[21] Appl. No.: 611,276

[22] Filed: May 17, 1984

[51] Int. Cl.$^4$ .............................................. C07K 71/00
[52] U.S. Cl. .................................................... 560/339
[58] Field of Search ..................... 260/453 P; 560/339

[56] References Cited

U.S. PATENT DOCUMENTS 3,920,644  11/1975  Handa et al. ..................... 260/453 P
3,948,966   4/1976  Inamoto et al. ................... 260/453 P
4,361,518  11/1982  Singh et al. ...................... 260/453 P Primary Examiner—Alan Siegel
Attorney, Agent, or Firm—Steven H. Flynn

[57] ABSTRACT

A process for forming useful oligomers and higher homopolymers of 1,3- or 1,4-bis(1-chloro-1-methylethyl)benzene is disclosed which comprises polymerizing a 1,3- or 1,4-bis(1-chloro-1-methylethyl)benzene and an alkali metal or an alkaline earth metal cyanate in a solvent for the organic reactant and the substantial absence of a catalyst at temperatures of between about 15° C. and about 60° C. until formation of the oligomers and homopolymers is substantially complete. The oligomers and homopolymers produced are related to poly-TMI type polymers and are useful together with active polyurethane coating and/or injection moldable compositions.

9 Claims, No Drawings

PROCESS FOR THE PREPARATION OF POLYMERIC TERTIARY ARALKYL ISOCYANATES FROM 1,3- OR 1,4-BIS(1-CHLORO-1-METHYLETHYL)BENZENE

The present invention relates to a process for preparing polymeric tertiary aralkyl isocyanates for use in polyurethane resin compositions and urethane resin applications. More particularly, it relates to a process for forming oligomers or homopolymers from 1,3- or 1,4-bis(1-chloro-1-methylethyl)benzene and alkali metal or alkaline earth metal salts of isocyanic acid in the substantial absence of a catalyst at temperatures of between about 15° C. and about 60° C.

Alkenyl tertiary aralkyl isocyanate compounds, such as, meta-isopropenyl-$\alpha,\alpha$-dimethylbenzylisocyanate (m-TMI) and para-isopropenyl-$\alpha,\alpha$-dimethylbenzylisocyanate (p-TMI), are presently known. It is disclosed in U.S. application Ser. No. 400,799, filed July 22, 1982, assigned to the same assignee as the present invention and now allowed, that m-TMI and p-TMI are formed as by-products of a thermal cracking reaction of tertiary aralkyl biscarbamates to form useful tertiary aralkyl isocyanate compounds.

The m-TMI and p-TMI compounds have substantial utility per se as distinct products by virtue of their difunctional character, e.g., they possess both a reactive isocyanate group (—NCO) as well as ethylenic unsuturation. The m-TMI and p-TMI compounds may be homopolymerized or copolymerized to form polymers posesssing isocyanate functionality, i.e., polymers having pendant isocyanato groups along the polymer chain. The m-TMI and p-TMI polymers or copolymers may thereafter be crosslinked with curing agents in the form of compounds having a plurality of reactive hydrogens, such as difunctional or polyfunctional amines or alcohols. The cross-linkable compositions have film forming properties and may advantageously be used in coatings applications on metal, wood and glass substrates, or may be employed to form molded articles, for example, in accordance with reaction injection molding techniques.

It is presently known that oligomers and homopolymers of m-TMI and p-TMI compounds may be prepared by various methods. In U.S. Pat. No. 3,290,350, for example, it is disclosed that TMI compounds may be polymerized by employing conventional addition polymerization initiators of the free radical type, such as peroxy or azo initiators, at low temperatures. More particularly, this patent discloses homopolymerization of m-TMI in a solvent mixture with isooctane containing boron trifluoride etherate at a polymerization temperature of −72° C. The polymerized mixture is allowed to equilibrate at room temperature and the polymer is isolated after three days. The isolated homopolymer described therein has a softening temperature of about 60° C. and a molecular weight of about 1500, being soluble in dimethylformamide and insoluble in xylene.

Another method for forming oligomers and homopolymers of alkenyl tertiary aralkyl isocyanate compounds which are soluble in aromatic hydrocarbon solvents is disclosed in copending U.S. application Ser. No. 499,921, filed June 1, 1983, assigned to the same assignee as the present invention. As disclosed in said application, a process for forming oligomers or higher homopolymers of m- or p-TMI comprises solution polymerizing m- or p-TMI in a solvent selected from methylene chloride and/or toluene at temperatures of between about −80° C. to about −25° C. in the presence of a Bronsted acid or Lewis acid polymerization catalyst, such as anhydrous p-toluenesulfonic acid or stannic chloride, and thereafter neutralizing the polymerization catalyst at a temperature of from about −80° C. to about 10° C. with, for example, pyridine to prevent substantial formation of isocyanic acid. Additionally, it is disclosed that controlled molecular weight oligomers having peak molecular weights in the range of from about 4,000 to about 12,000 may be prepared by solution polymerizing TMI in methylene chloride with a catalytic amount of stannic chloride in the presence of a tertiary benzylic chloride compound added as a chain-transfer agent at temperatures of −25° C. or less, followed by catalyst neutrlization with pyridine at temperatures of −25° C. or less. The application discloses that temperatures of 10° C. or higher are to be avoided in the solution polymerization step, because higher temperatures promote elimination of isocyanic acid from the TMI monomer, resulting in little or no polymerization due to catalyst deactivation by the isocyanic acid.

A major shortcoming of each of the above-described prior art methods for forming oligomers and homopolymers of TMI is that extremely low reaction temperatures need to be employed. Moreover, added catalysts are needed and a catalyst neutralization step, in the latter method, is required.

Unexpectedly, in view of the foregoing, it has now been discovered that useful oligomers and higher homopolymers, similar to those based on TMI units, and possessing high tertiary aralkyl isocyanate functionality may be prepared in good yield by reacting 1,3- or 1,4-bis(1-chloro-1-methylethyl)benzene and an alkali metal or alkaline earth metal salt of cyanic acid in a suitable solvent for the organic reactant, at about room temperatures, without the need to use added catalysts or undesirably low reaction temperatures.

It has now surprisingly been discovered that mixtures of 1,3- or 1,4-bis(1-chloro-1-methylethyl)benzene in a solvent and alkali metal or alkaline earth metal salts of isocyanic acid react at room temperature in the substantial absence of a catalyst to form useful oligomers or higher homopolymers based on units similar to m-TMI or p-TMI units, having high isocyanate functionality. More particularly, the present invention provides a process for the preparation of oligomers and homopolymers from 1,3- or 1,4-bis(1-chloro-1-methylethyl)benzene, said process comprising polymerizing a 1,3- or 1,4-bis(1-chloro-1-methylethyl)benzene and an alkali metal or alkaline earth metal salt of isocyanic acid in the substantial absence of a catalyst at temperatures of between about 15° C. and 60° C. until formation of said oligomers and homopolymers is substantially complete.

In preferred embodiments, the metal isocyanate salt used is sodium cyanate. Suitable solvents for use in the process of the present invention may be selected from alkyl halides, such as methylene chloride and 1,2-dichloroethane, and aromatic hydrocarbon solvents such as benzene, chlorobenzene, toluene, xylene or the like. The preferred solvent for use in the process of this invention is methylene chloride.

The polymerizable solution of the present invention is simply and easily reacted by stirring at about room temperature, e.g., at a temperature between about 15° C. and about 60° C., for a time sufficient to permit the polymerization reaction to proceed to substantial completion. Typically, and without limitation, the reactants will be stirred at room temperature for a period of from 5 to about 30 hours, and preferably for a period of from about 15 to about 25 hours. Generally, and without limitation, the polymerization reaction proceeds with broad ranges of the starting materials and typically the molar ratios of 1,3- or 1,4-bis(1-chloro-1-methylethyl)-benzene to alkali metal or alkaline earth metal cyanate salt employed may range from about 1:1 to about 10:1, respectively.

The reaction in accordance with the process of the present invention proceeds slowly and spontaneously at room temperatures in the substantial absence of a catalyst to yield an insoluble alkali or alkaline earth metal chloride precipitate; minor amounts of m- or p-isopropenyl-α,α-dimethylbenzylisocyanate (m- or p-TMI) and m- or p-tetramethylxylylenediisocyanate (m- or p-TMXDI); and oligomers and homopolymers based on 1,3- or 1,4-bis(1-chloro-1-methylethyl)benzene units, having tertiary aralkyl isocyanate functionality and some unsaturation. The oligomers and homopolymers are produced in the form of a broad range of higher oligomeric materials peaking at molecular weights of approximately 2500.

In accordance with the new and improved process of the present invention useful oligomers and higher homopolymers of 1,3- or 1,4-bis(1-chloro-1-methylethyl)-benzene are prepared without the need to use added catalysts or extremely low reaction temperatures on the order of about −80° C. to about −25° C. as was required for the processes of the prior art which is unexpected. In accordance with the process of the present invention, by selection of suitable starting materials, a series of reactions proceeds which favors formation of the useful and desirable oligomers and homopolymers in good yields without the cumbersome reaction restrictions of low temperature and catalyst heretofore required.

Other objects and advantages of the present invention will become apparent from the following detailed description of the invention, together with the illustrative working examples.

In accordance with the process of the present invention, the 1,3- or 1,4-bis(1-chloro-1-methylethyl)benzene-derived oligomers and homopolymers are prepared by polymerizing a solution which first comprises a compound selected from 1,3-bis(1-chloro-1-methylethyl)benzene and 1,4-bis(1-chloro-1-methylethyl)benzene, e.g. compounds having the formula:

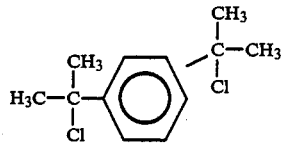

The 1,3- or 1,4-bis(1-chloro-1-methylethyl)benzene starting materials may be easily prepared in accordance with known methods, such as for example by reacting m- or p-diisopropenylbenzene with hydrogen chloride.

The polymerizable mixture in accordance with the process of this invention comprises the organic reactant in a solvent and an alkali metal or alkaline earth metal salt of isocyanic acid which usually is not dissolved. More particularly, the alkali metal or alkaline earth metal cyanate salts for use herein may comprise metal cyanate salts of the alkali metals, e.g., sodium, lithium, potassium, rubidium and cesium or salts of the alkaline earth metals, e.g., calcium, barium, and strontium. These metal cyanate salts are well known. The preferred metal isocyanate salt for use herein is sodium cyanate which is abundantly available commercially.

In accordance with the present invention, the 1,3- or 1,4-bis(1-chloro-1-methylethyl)benzene dissolved in a suitable solvent, and an alkali metal or alkaline earth metal cyanate salt are mixed and reacted. Suitable solvents are alkyl halides such as methylene chloride and 1,2-dichloroethane and aromatic hydrocarbon solvents, such as benzene, toluene, xylene and the like. The preferred solvent is methylene chloride.

In accordance with the process of the present invention the solution is polymerized by reacting the starting materials at temperatures of between about 15° C. and 60° C. in the substantial absence of a catalyst until the polymerization is substantially complete. Typically, and without limitation, the reactants will be stirred at room temperature for a period of from about 5 to about 30 hours, and preferably for a period of from about 15 to about 25 hours. Generally, and without limitation, the polymerization reaction proceeds with broad ranges of the starting materials and typically the molar ratios of 1,3- or 1,4-bis(1-chloro-1-methylethyl)benzene to alkali metal or alkaline earth metal cyanate salt employed may range from about 1:1 to about 1:10, and preferably in the range from 1:2 to 1:4.

The reaction in accordance with the process of the present invention proceeds slowly and spontaneously at room temperatures in the substantial absence of a catalyst to yield insoluble alkali or alkaline earth metal chloride precipitate; minor amounts of m- or p-isopropenyl-α,α-dimethylbenzylisocyanate (m- or p-TMI) and m- or p-tetramethylxylylenediisocyanate (m- or p-TMXDI); and oligomers and homopolymers based on 1,3 or 1,4-bis(1-chloro-1-methylethyl)benzene units, having tertiary aralkyl isocyanate functionality and some unsaturation. The oligomers and homopolymers are produced in the form of a broad range of higher oligomer materials peaking at molecular weights of approximately 1500.

Without wishing to be bound, it is believed that the oligomers and higher homopolymers produced by the process of the present invention are similar in structure to poly-TMI polymers of the prior art, and generally may be represented by the formula:

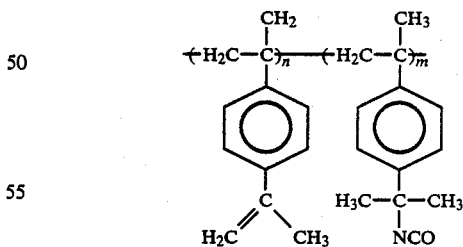

wherein n is 0 or an integer of from 1 to 20 and m is an integer of from 1 to 20 and the sum of n plus m is ≦20.

After the polymerization reaction is substantially complete, the oligomers and homopolymers may be isolated by filtering the product solution to remove insoluble solids and thereafter the solvent may be removed by evaporation at room temperature, or at elevated temperatures, at normal atmospheric pressures, or under a vacuum to yield the oligomer and homopolymer products.

The oligomeric and homopolymeric products of the process of the present invention may thereafter be employed to form useful urethane coating and/or injection moldable compositions in admixture with curing agents comprising compounds possessing active hydrogens, such as di- or polyfunctional amines or alcohols, in accordance with the methods described in the above-mentioned patent and application, in connection with poly-TMI polymers.

The following working examples are provided to better illustrate how the present invention may be practiced to those skilled in this art.

EXAMPLE 1

A mixture of 0.10 mole of 1,4-bis(1-chloro-1-methylethyl)benzene (p-TMXDC), 0.22 mole of sodium cyanate and 80 cc of $CH_2Cl_2$ was stirred at room temperature overnight. The product solution was then filtered from insoluble solids and was evaporated to a syrup. This was shown by gas phase chromatography to contain p-TMI and p-TMCDI amounting to 5% and 2% yields, respectively, based on the starting dichloride, and equivalent to 0.33 meq RNCO per g. However, the syrup was found to contain 1.51 meq RNCO/g (and 2.24 mmoles of unsaturation/g.) When the residual solvent is taken into account, the isocyanate content of the polymer present was calculated to be 1.8 meq/g with 3.4 mmoles of unsaturation/g.

Gel permeation chromatography indicated that the polymer consisted of a broad range of higher oligomeric material, peaking at 2500 M.W.

The oligomers and homopolymers prepared in accordance with the process of this invention are related to poly-TMI prepared by acid catalyzed polymerization under carefully controlled conditions. The oligomers and homopolymers produced herein may tend to be less light stable than poly-TMI because of the higher levels of unsaturation which they may contain. However, the isocyanate functionality of the oligomers and homopolymers may be used together with curing or crosslinking agents to form useful curable polyurethane resin compositions.

Each of the above-mentioned patents and applications are specifically incorporated herein by reference.

Although the present invention has been described with references to certain preferred embodiments, modifications or changes may be made therein by those skilled in this art without departing from the scope and spirit of the present invention, as defined by the following appended claims.

What is claimed is:

1. A process for the preparation of oligomers and homopolymers from 1,3- or 1,4-bis(1-chloro-1-methylethyl)benzene, said process comprising:

polymerizing a 1,3- or 1,4-bis(1-chloro-1-methylethyl)benzene and an alkali metal or alkaline earth metal cyanate in a solvent for the organic reactant and in the substantial absence of a catalyst at temperatures of between about 15° C. and about 60° C. until formation of said oligomers and homopolymers is substantially complete.

2. A process as recited in claim 1, wherein the alkali metal or alkaline earth metal cyanate is sodium cyanate.

3. A process as recited in claim 1, wherein the solvent is selected from alkyl chlorides or aromatic hydrocarbon solvents.

4. A process as recited in claim 1, wherein the solvent is methylene chloride.

5. A process as recited in claim 1, wherein the molar ratio of said 1,3- or 1,4-bis(1-chloro-1-methylethyl)benzene to said metal cyanate in said solution is from about 1:1 to about 1:10, respectively.

6. A process as recited in claim 1, wherein the solution is stirred at a temperature of between about 15° C. and 60° C. for a period of from about 5 to about 30 hours.

7. A process as recited in claim 1, wherein the solution is polymerized for a time sufficient to form oligomers and homopolymers having molecular weights of above about 1,000.

8. A process as recited in claim 1, further comprising the step of separating the oligomer and homopolymer product solution from insoluble solids by filtration.

9. A process as recited in claim 8, further comprising the step of removing the solvent from said solution.

* * * * *